United States Patent [19]
Janssen et al.

[11] Patent Number: 6,121,503
[45] Date of Patent: *Sep. 19, 2000

[54] PRODUCTION OF HIGH PURITY OLEFINS

[75] Inventors: Marcel Johannes Gerardus Janssen; James Andrew Zboray, both of Houston, Tex.

[73] Assignee: Exxon Chemical Pateuts Inc., Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/980,174

[22] Filed: Nov. 26, 1997

Related U.S. Application Data

[63] Continuation of application No. 08/980,174, Nov. 26, 1997, abandoned, which is a continuation of application No. 08/611,976, Mar. 6, 1996, abandoned, which is a continuation of application No. 08/277,129, Jul. 19, 1994, abandoned, which is a continuation of application No. 07/889,691, May 27, 1992, abandoned.

[51] Int. Cl.$^7$ ................. C07C 1/02; C07C 1/20
[52] U.S. Cl. ............ 585/640; 585/638; 585/639
[58] Field of Search .................. 585/640, 638, 585/639

[56] References Cited

U.S. PATENT DOCUMENTS

| | | | |
|---|---|---|---|
| 4,359,595 | 11/1982 | Rollmann | 585/640 |
| 4,638,106 | 1/1987 | Pieters et al. | 585/640 |
| 4,677,243 | 6/1987 | Kaiser | 585/638 |
| 5,077,026 | 12/1991 | Nair et al. | 423/326 |
| 5,095,163 | 3/1992 | Berger | 585/640 |

FOREIGN PATENT DOCUMENTS 0 642 485 B1  8/1996  European Pat. Off. .

OTHER PUBLICATIONS

Chemical Industry of Natural Gas [Tian Ran Qi Hua Gong] vol. 20, No. 5, 1995.
Decision Revoking the European Patent for European Patent No. 0642485.
Kirk–Othmer, "Encyclopedia of Chemical Technology," 3d Ed., vol. 9, pp. 408–413, 1982.
Kirk–Othmer, "Encyclopedia of Chemical Technology," 3d Ed., vol. 19, pp. 232–235, 1982.
Kirk–Othmer, "Encyclopedia of Chemical Technology," 4$^{th}$ Ed., vol. 9, pp. 894–905, 1996.
Kirk–Othmer, "Encyclopedia of Chemical Technology," 4$^{th}$ Ed., vol. 20, pp. 255–260, 1996.
Ullman's Encyclopedia of Industrial Chemistry, 5$^{th}$ Ed., vol. A10, pp. 78–86, 1987.
Ullman's Encyclopedia of Industrial Chemistry, 5$^{th}$ Ed., vol. A22, pp. 213–219, 1987.
EPO Communication with Summons to Attend Oral Proceedings Pursuant to Rule 71(1) EPC.
Vora et al., "Conversion of Natural Gas to Ethylene and Propylene: UOP/HYDRO MTO Process," 2d International Petroleum Conference and Exhibition, Jan. 1997.
Gregor, "Adding Value to Methanol: UOP/HYDRO MTO Process," 1996 World Methanol Conference, Dec. 1996.
Barger et al., "Hydrothermal Stability of SAPO–34 in the Methanol–to–Olefins Process", The Arabian Journal for Science and Engineering, vol. 21, No. 2, pp. 263–272, Apr. 1996.
Vora et al., "Conversion of Methanol to Ethylene and Propylene with the UOP/HYDRO MTO Process," RPL Asia 96, Sep. 1996.
Vora, et al., "UOP/HYDRO MTO Process the Critical Line in Upgrading Natural Gas to Olefins," 1996 Dewitt Petrochemical Review, Mar. 1996.
UOP Notice of Opposition to EP 0 642 485 B! and supporting references.
Exxon Chemical's Response to UOP Opposition Documents.
UOP Rebuttal Response to Exxon Chemical's Response and attachments.

*Primary Examiner*—Marian C. Knode
*Assistant Examiner*—Tam M. Nguyen
*Attorney, Agent, or Firm*—Linda Russell; Bradley A. Keller

[57] ABSTRACT

A process for converting an oxygenate feed to high purity olefins such as polymer-grade propylene ($C_3^0/C_3^= \leq 0.05$) at a temperature of about 450° C. (842° F.), using a molecular sieve catalyst having a high preselected $Si/Al_2$ ratio (such as ZSM-5, ZSM-48) or a preselected $Si/Fe_2$ ratio (such as FeZSM-5), or SAPO-34.

7 Claims, No Drawings

PRODUCTION OF HIGH PURITY OLEFINS

CROSS REFERENCE TO RELATED APPLICATIONS

The present application is a continuation of U.S. patent application Ser. No. 08/980,174 filed Nov. 26, 1997, now abandoned, which was a continuation of U.S. patent application Ser. No. 08/611,976 filed Mar. 6, 1996, now abandoned, which was a continuation of U.S. patent application Ser. No. 08/277,129 filed Jul. 19, 1994, now abandoned. U.S. patent application Ser. No. 08/277,129 was a continuation of U.S. patent application Ser. No. 07/889,691 which was filed May 27, 1992 and is now abandoned.

BACKGROUND OF THE INVENTION

This invention relates to a process for converting an oxygenate to high purity olefins by contacting the oxygenate with a molecular sieve catalyst. More particularly, the invention relates to a process for converting a methanol or methanol-water mixture to polymer-grade propylene by contacting the feed with zeolite or silicoaluminophosphate catalysts.

High purity olefins such as propylene have traditionally been produced through the process of steam and/or catalytic cracking. Because of the limited availability and high cost of petroleum sources, the cost of producing high purity olefins from such petroleum sources has been steadily increasing. Curtailment in the availability of inexpensive petroleum raw materials threatens the supply of high purity olefins such as polymer-grade propylene. Polymer-grade propylene is used in the production of many types of plastics such as polypropylene.

The search for alternative materials for high purity olefin production has led to the use of oxygenates such as alcohols, and more particularly to methanol and higher alcohols or their derivatives. These alcohols may be produced by fermentation or from synthesis gas. Synthesis gas can be produced from natural gas, petroleum liquids, carbonaceous materials including coal, recycled plastics, municipal wastes, or any organic material. Thus, alcohol and alcohol derivatives may provide non-petroleum based feeds for high purity olefin production.

Molecular sieves, such as crystalline zeolite catalysts, are known to promote the conversion of oxygenates to olefin-containing hydrocarbon mixtures. U.S. Pat. No. 4,025,575 and U.S. Pat. No. 4,083,889 disclose processes for conversion of methanol and/or methyl ether to olefin-containing products using ZSM-5-type zeolite catalysts.

Chang et al., U.S. Pat. No. 4,724,270, describe a process for converting methanol feedstocks to aromatic hydrocarbons using zeolite catalysts (having a silica-to-alumina ratio of at least 12) at a temperature of at least 725° C. (1337° F.). By conducting the reaction at elevated temperatures, zeolite dehydroxylation can occur. This can lead to zeolite decomposition to amorphous silica and alumina.

U.S. Pat. No. 4,433,189 to Young teaches conversion of methanol to light olefins over zeolite catalysts having a silica-to-alumina molar ratio of at least 12, and at a temperature of from about 200° C. (392° F.) to 500° C. (932° F.). The Young patent does not teach conversion of methanol to products such as polymer-grade propylene.

U.S. Pat. No. 4,677,243 to Kaiser teaches the formation of light olefins using silicoaluminophosphate catalysts at a temperature of from about 200° C. (392° F.) to 700° C. (1292° F.). Kaiser does not teach the formation of high purity olefins or polymer-grade propylene.

High purity olefins are generally recognized by those skilled in the art as products, excluding methane, which have a paraffin-to-olefin weight ratio of less than or equal to about 0.05. Purification of high purity olefins traditionally requires removal of low-level impurities which interfere with polymerization catalysis, or which interfere with other processes requiring high-purity reactants. Low-level contaminants include, but are not limited to, polar molecules, oxygenates such as water, alcohols, carbon monoxide, carbon dioxide, carbonyl sulfide (COS), oxygen, and other miscellaneous contaminants including hydrogen sulfide, mercaptans, ammonia, arsine phosphine, chlorides, etc. Low-level contaminants are removed by a variety of processes including, but not limited to adsorption and fractional distillation. Lighter or heavier hydrocarbon molecules having fewer or more carbon atoms than the desired olefin product must also be removed. These hydrocarbons are typically removed by fractional distillation techniques.

One such high purity olefin is polymer-grade propylene. Polymer-grade propylene is required for the production of polypropylene and useful for the production of other propylene derivatives. Polymer-grade propylene is characterized by very low concentrations of impurities, including low levels of paraffins (saturated hydrocarbons) such as propane, ethane, and butane.

Commercial chemical-grade propylene, unlike polymer-grade propylene, is characterized by higher concentrations of saturated hydrocarbons. Propane is the most difficult of the saturated hydrocarbons to remove from propylene, due in large part to the proximity of the boiling points for propane and propylene. Typical polymer-grade propylene purities range from 95% to 99.5% propylene, and are more preferably above 99%. This degree of purity corresponds to propane-to-propylene ratios of about 0.05 to about 0.01 or lower. Before the teachings of the present invention, this low propane level could only be practically achieved through the use of the well known art of fractional distillation. The fractional distillation scheme employed for effecting the difficult separation of propane from propylene is called "superfractionation." However, superfractionation requires a substantial investment in facilities and consumes copious amounts of energy. Alternative means for removing paraffin impurities, such as membrane techniques and adsorbent techniques, are as costly as the superfractionation techniques. The present invention teaches a means for producing high purity olefins having the required range of paraffin-to-olefin ratios, without the need to resort to superfractionation or other expensive purification techniques. According to the teachings of the present invention, a superfractionator is not required, thereby significantly reducing the cost of producing high purity olefins such as polymer-grade propylene.

These and other disadvantages of the prior art are overcome by the present invention, and a new, improved process for selectively converting oxygenates to high purity olefins is provided.

SUMMARY OF THE INVENTION

In accordance with the present invention, a process is provided for the selective conversion of an oxygenate to high purity olefins, and more particularly to polymer-grade propylene. The process employs molecular sieves such as the crystalline aluminosilicate, ferrosilicate zeolites, and silicoaluminophosphate (SAPO) catalysts. Preferred embodiments employ ZSM-5, ZSM-48, FeZSM-5, and SAPO-34 as the molecular sieve. The reaction is conducted at a temperature of preferably about 450° C. (842° F.).

Oxygenate conversion under such conditions produces a product, substantially rich in high purity olefins, such as polymer-grade propylene.

It is an object of the present invention to describe a process for selectively catalytically converting oxygenates to high purity olefins, comprising, contacting the oxygenate with a molecular sieve having a preselected silica-to-metal ($Me_2O_3$) ratio, a preselected WHSV, and at a temperature of about 350° C. (662° F.) to about 550° C. (1022° F.), and recovering the high purity olefins.

By employing the teachings of the present invention, a person having ordinary skill in the catalysis or olefin art should be able to produce a high purity olefin product from oxygenates without resorting to purification techniques such as adsorption or superfractionation. However, it is within the scope of the present invention to include such additional purification techniques should the person practicing this invention desire to produce olefins having even higher degrees of purity than high purity olefins.

These and other advantages of the present invention will become apparent from the following detailed description.

DETAILED DESCRIPTION OF THE INVENTION

In accordance with the present invention, an oxygenate feed is catalytically converted to high purity olefins by contacting this feed with a molecular sieve zeolite and/or silicoaluminophosphate catalyst. The method of the present invention obviates the need for a conventional superfractionator to separate paraffins from olefins. It is within the scope of the present invention to use additional purification steps well known in the art to remove impurities other than paraffins having the same number of carbon atoms as olefins. Additionally, superfractionation may be used with the present invention to achieve still higher degrees of olefin purity. More particularly, the present invention relates to a process for catalytically converting oxygenates to high purity olefins such as polymer-grade propylene.

Zeolites are a class of molecular sieve catalysts and are porous, crystalline-hydrated metallo-silicates of Group IIIA and VIII elements interconnected through shared oxygen atoms. Preferable metals include aluminum, iron, gallium, nickel, cobalt, and boron. The rigid three dimensional network of silica and metal (hereinafter "$Me_2O_3$") creates a tetrahedral form which comprises the primary building unit of the zeolites. The metal constituents in zeolites include, but are not limited to, aluminum, iron, gallium, and boron. Because the oxygen atoms in zeolites are shared by tetrahedra, the framework possesses a net negative charge.

For example, the net negative charge of aluminosilicate zeolites is balanced by exchangeable cations in the crystalline structure, leading to the representation:

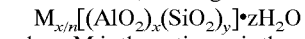

where M is the cation, n is the cation charge, and z represents the water of hydration. The silica-to-alumina molar ratio is controlled by the amounts of alumina "x" and silica "y" in the zeolite. When M is a proton, the zeolite acquires the characteristics of a Broensted acid (e.g., HZSM-5).

Other positive ion-containing catalysts include ferrosilicates, borosilicates, and gallosilicates. Of the ferrosilicates, FeZSM-5 may be employed in the process of the present invention. FeZSM-5 is composed of silicon and iron oxide ($Fe_2O_3$) in a manner similar to the aluminosilicate zeolites.

Zeolites generally have ordered, porous crystalline structures containing a small number of cavities that are interconnected by a number of still smaller channels. The cavities and channels are uniform in size within a certain type of zeolitic material. The dimensions of the pores or cavities allow for adsorption of molecules of certain dimensions while excluding molecules of larger dimensions. The crystal structure of zeolites provides a selective constrained access to and egress from the intracrystalline free space. This phenomenon, also called "shape-selective catalysis," derives from zeolite geometry.

An important component of zeolite geometry derives from the proportions of silicon and $Me_2O_3$ atoms comprising the tetrahedra. The molar ratio of silica-to-$Me_2O_3$ may be determined by conventional analysis, such as wet chemical analysis (e.g., Atomic Absorption Spectrometry or Inductively Coupled Plasma Emission Spectrometry;) or by the stoichiometry of silica and $Me_2O_3$ used to synthesize the zeolite. The silica-to-$Me_2O_3$ molar ratio is meant to represent, as closely as possible, the silica-to-$Me_2O_3$ ratio in the rigid anionic framework of the molecular sieve crystal. $Me_2O_3$ in the binder or in cationic or other form within the porous channels is not considered in calculating the silica-to-$Me_2O_3$ ratio. The ratio of silica-to-$Me_2O_3$ in the molecular sieve imparts selective catalytic and adsorptive properties. The catalytic and adsorptive properties of the molecular sieve may also be varied by changing the ions within the catalyst. Conventional ion exchange techniques may be used to change the cations.

To those skilled in the zeolite catalyst art, ZSM-5 is generally considered a siliceous zeolite. This is because it may have a "high" silica-to-$Me_2O_3$, or more specifically, silica-to-alumina molar ratio. ZSM-5 is particularly advantageous for converting methanol-containing feedstocks to light olefins. Siliceous zeolites (i.e., zeolites having a high silica-to-$Me_2O_3$ ratio), such as those described for use in the processes of the present invention, are most effectively synthesized using templates such as alkylammonium cations. For example, the tetramethylammonium (TMA) cation is particularly advantageous in synthesizing a siliceous zeolite such as ZSM-5 having a silica-to-alumina ratio of about 1000. It is thought that silica forms hydrogen bonds with the TMA and traps or clathrates the organic cation within the silica. Alumina is less efficient in hydrogen bond formation, so the zeolites formed with organic templates such as TMA have a higher silica-to-alumina molar ratio. The presence of a trivalent metal site within the silicate structure provides the desired acidity in an environment which limits access to the site by molecules of appropriate size. This limits the acid catalyzed reactions to those which are carried out in a "shape selective" manner. Template cations which are usually present in these materials when they are synthesized may be removed, and the zeolite converted to the hydrogen form by exchange with ammonium ions, followed by heating to drive off ammonia, or by direct exchange with an acid such as hydrochloric acid, provided the zeolite is not degraded by the acidic treatment.

The silicoaluminophosphate (SAPO) molecular sieve catalysts exhibit properties characteristic of both aluminosilicate zeolites and aluminophosphates. The SAPO molecular sieves have a microporous crystal framework structure of $PO_2^+$, $AlO_2^-$ and $SiO_2$ tetrahedral units. The composition (anhydrous) is:

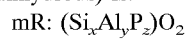

wherein "R" represents at least one organic templating agent present in the intracrystalline pore system, "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular SAPO species involved, and "x," "y," and "z" represent the mole fractions of silicon, aluminum, and phosphorous, respectively. Representative SAPO molecular sieves, as described in U.S. Pat. No. 4,440,871 (and incorporated herein by reference), include SAPO-5, SAPO-11, SAPO-17, SAPO-20, SAPO-31, SAPO-34, SAPO-35, SAPO-37, SAPO-40, SAPO-41, and SAPO-42.

The oxygenate feed comprises hydrocarbons containing aliphatic moieties such as, but not limited to, alcohols, halides, mercaptans, sulfides, amines, ethers, and carbonyl compounds (aldehydes, ketones, carboxylic acids, and the like) or mixtures thereof. The aliphatic moiety preferably contains from about 1 to about 10 carbon atoms, and more preferably 1 to 4 carbon atoms. Representative oxygenates include methanol, isopropanol, n-propanol, ethanol, fuel alcohols, dimethyl ether, diethyl ether, methyl mercaptan, methyl sulfide, methyl amine, ethyl mercaptan, ethylchloride, formaldehyde, dimethylketone, acetic acid, n-alkylamines, n-alkylhalides, and n-alkylsulfides having alkyl groups of 1 to 10 carbon atoms or mixtures thereof. In a preferred embodiment of the present invention, the feed comprises methanol. In another embodiment, the methanol feed contains a diluent. The addition of a diluent to the total feed charge decreases paraffin production relative to olefin production.

The term "oxygenate feed" as employed in the present invention and described herein designates only the organic material used as the feed. However, the total charge to the reaction zone may contain additional compounds such as diluents. Use of a diluent as part of the feed, which is miscible with the oxygenate, imparts as a non-limiting example, a smaller propane to propylene ($C_3^0/C_3^=$) ratio than the use of essentially anhydrous oxygenate. However, even anhydrous oxygenates contain trace quantities of diluents. Even though the process described herein may employ a diluent, computable quantities of the oxygenate feed (i.e, composition and Weight Hourly Space Velocity (WHSV)) are to be computed as an essentially diluent-free oxygenate feed unless otherwise stated.

The process is generally conducted in the presence of one or more diluents which may be present in the feed in an amount between about 1 and about 99 molar percent, based on the total number of moles of all feed and diluent components fed to the reaction zone (or catalyst). The amount of diluent added to the oxygenate feed will depend in part on the type of catalyst selected, the silica-to-$Me_2O_3$ ratio, and the reaction temperature. Preferably, the molar ratio of oxygenate feed-to-diluent (feed:diluent) is about 1:1 to about 1:4. Diluents include, but are not limited to, helium, argon, nitrogen, carbon monoxide, carbon dioxide, hydrogen, water, paraffins, hydrocarbons (such as methane and the like), aromatic compounds, and mixtures thereof. Preferably, the diluent is water.

The instant process is preferably conducted in the vapor phase such that the oxygenate feed is contacted in the vapor phase in a reaction zone with the molecular sieve at effective process conditions to produce a propane/propylene ratio characteristic of high purity olefins or polymer-grade propylene, i.e., an effective temperature, silica-to-$Me_2O_3$ ratio, pressure, WHSV and, optionally, an effective amount of diluent, correlated to produce high purity olefins or polymer-grade propylene. Alternatively, the process may be conducted in a liquid phase.

The process is effectively carried out over a wide range of pressures including autogeneous pressures. At pressures between about 0.001 atmospheres (0.76 torr) and about 1000 atmospheres (760,000 torr), the formation of light olefin products will be effected although the optimum amount of product will not necessarily form at all pressures. The preferred pressure is between about 0.01 atmospheres (7.6 torr) and about 100 atmospheres (76,000 torr). The pressures referred to herein for the process are exclusive of the inert diluent, if any, that is present, and refer to the partial pressure of the feedstock as it relates to oxygenate compounds and/or mixtures thereof. Pressures outside the stated range are not excluded from the scope of this invention, although such pressures do not fall within certain desirable embodiments of the invention. At the lower and upper end of the pressure range, and beyond, the selectivities, conversions, and/or rates to light olefin products may not be optimal, although light olefins such as ethylene may still be formed.

The process is effected for a period of time sufficient to produce the desired light olefin (and high purity olefin) products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor), and process design characteristics selected.

The olefin production process may be carried out in a batch, semi-continuous, or continuous fashion. The process can be conducted in a single reaction zone, or a number of reaction zones arranged in series or in parallel, or it may be conducted intermittently or continuously in an elongated tubular zone or a number of such zones. When multiple reaction zones are employed, it may be advantageous to employ one or more of such molecular sieves in series to provide for a desired product mixture. Owing to the nature of the process, it may be desirous to carry out the process of the present invention by use of the molecular sieve catalysts in a dynamic (e.g., fluidized or moving) bed system or any system of a variety of transport beds rather than in a fixed bed system. Such systems would readily provide for any regeneration (if required) of the molecular sieve catalyst after a given period of time. If regeneration is required, the molecular sieve catalyst can be continuously introduced as a moving bed to a regeneration zone where it can be regenerated, such as for example by removing carbonaceous materials or by oxidation in an oxygen-containing atmosphere. In the preferred practice of the invention, the catalyst will be subject to a regeneration step by the burning of carbonaceous deposits accumulated during reactions.

The effect of feedstock flow rate over molecular sieves is well known to those skilled in the art. Increasing the flow rate (WHSV) enhances olefin production relative to paraffin production. However, the enhanced olefin production relative to paraffin production is offset by a diminished conversion of oxygenate to hydrocarbons at the higher flow rates.

The process for conversion of an oxygenate feed to high purity olefins using molecular sieves is conducted at temperatures of from approximately 350° C. (662° F.) to about 550° C. (1022° F.), preferably about 450° C. (842° F.) to about 550° C. (1022° F.), and more preferably at about 440° C. (824° F.) to about 460° C. (860° F.). The silica-to-$Me_2O_3$ molar ratio is preselected according to the type of molecular sieve employed, the reaction temperature used, and the degree of high purity olefin production required. The WHSV of this reaction is approximately 0.01 hr.$^{-1}$ to about 100 hr.$^{-1}$, preferably about 0.5 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs.

The process for conversion of an oxygenate feed to polymer-grade propylene using molecular sieves is conducted at temperatures of from approximately 350° C. (662° F.) to about 550° C. (1022° F.), preferably about 450° C. (842° F.) to about 550° C. (1022° F.), and more preferably at about 440° C. (842° F.) to about 460° C. (860° F.). The silica-to-Me$_2$O$_3$ molar ratio is preselected according to the type of molecular sieve employed, the reaction temperature used, and the degree of polymer-grade propylene production required. The WHSV of this reaction is approximately 0.01 hr.$^{-1}$ to about 100 hr.$^{-1}$, preferably about 0.5 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs.

ZSM-5 is described in U.S. Pat. No. 3,702,886. The process for conversion of an oxygenate feed to high purity olefins using ZSM-5 is conducted at temperatures of approximately 350° C. (662° F.) to about 550° C. (1022° F.), preferably about 400° C. (752° F.) to about 550° C. (1022SF), and more preferably at about 440° C. (824° F.) to about 460° C. (860° F.). The silica-to-Me$_2$O$_3$ molar ratio is about 350 to about 2500, and preferably is about 950 to about 1050. The WHSV of this process is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs.

ZSM-5 is described in U.S. Pat. No. 3,702,886. The process for conversion of an oxygenate feed to polymer-grade propylene using ZSM-5 is conducted at temperatures of approximately 350° C. (662° F.) to about 550° C. (1022° F.), preferably about 400° C. (752° F.) to about 550° C., and more preferably at about 440° C. to about 460° C. (860° F.). The silica-to-Me$_2$O$_3$ molar ratio is about 350 to about 2500, and preferably is about 950 to about 1050. The WHSV of this process is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs.

ZSM-48 is described more fully in U.S. Pat. No. 4,397,827. The process for conversion of an oxygenate feed to high purity olefins using ZSM-48 is conducted at temperatures of approximately 350° C. (662° F.) to about 550° C. (1022° F.), preferably about 400° C. (752° F.) to about 550° C. (1022° F.), and more preferably at about 440° C. (824° F.) to about 460° C. (860° F.). The silica-to-Me$_2$O$_3$ molar ratio is about 300 to about 2500, and preferably is about 320 to about 353. The WHSV of this process is approximately 0.01 hr.$^{-1}$ to about 100 hr.$^{-1}$, preferably about 0.5 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs, comprising approximately 30% propylene and <1% propane.

ZSM-48 is described more fully in U.S. Pat. No. 4,397,827. The process for conversion of an oxygenate feed to polymer-grade propylene using ZSM-48 is conducted at temperatures of approximately 350° C. (662° F.) to about 550° C. (1022° F.), preferably about 400° C. (752° F.) to about 550° C. (1022° F.), and more preferably at about 440° C. (824° F.) to about 460° C. (860° F.). The silica-to-Me$_2$O$_3$ molar ratio is about 300 to about 2500, and preferably is about 320 to about 353. The WHSV of this process is approximately 0.01 hr.$^{-1}$ to about 100 hr.$^{-1}$, preferably about 0.5 hr.$^{-1}$ to about 10 hr.$^{-1}$, and more preferably about 0.8 hr.$^{-1}$ to about 1.2 hr.$^{-1}$. At about 0.8 to about 1.2 hr.$^{-1}$, approximately 98% to 100% conversion of the feed to hydrocarbons occurs, comprising approximately 30% propylene and <1% propane.

FeZSM-5 is described in U.S. Pat. No. 4,843,183. The process for conversion of an oxygenate feed to high purity olefins using FeZSM-5 is conducted at temperatures of approximately 350° C. (662° F.) to about 550° C. (1022° F.), preferably about 400° C. (752° F.) to about 550° C. (1022° F.), and more preferably at about 440° C. (824° F.) to about 460° C. (860° F.). The silica-to-Me$_2$O$_3$ molar ratio is about 332 to about 368, and preferably is about 350. The WHSV of this process is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs, comprising approximately 25% propylene with no propane production.

FeZSM-5 is described in U.S. Pat. No. 4,843,183. The process for conversion of an oxygenate feed to polymer-grade propylene using FeZSM-5 is conducted at temperatures of approximately 350° C. (662° F.) to about 550° C. (1022° F.), preferably about 400° C. (752° F.) to about 550° C. (1022° F.), and more preferably at about 440° C. (824° F.) to about 460° C. (860° F.). The silica-to-Me$_2$O$_3$ molar ratio is about 332 to about 368, and preferably is about 350. The WHSV of this process is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs, comprising approximately 25% propylene with no propane production.

SAPO-34 is described in U.S. Pat. No. 4,440,871. The process for conversion of an oxygenate feed to high purity olefins using SAPO-34 is conducted at temperatures of approximately 350° C. (662° F.) to about 550° C. (1022° F.), preferably about 400° C. (752° F.) to about 550° C. (1022° F.), and more preferably at about 440° C. (824° F.) to about 460° C. (860° F.). The WHSV of this process is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs.

SAPO-34 is described in U.S. Pat. No. 4,440,871. The process for conversion of an oxygenate feed to polymer-grade propylene using SAPO-34 is conducted at temperatures of approximately 350° C. (662° F.) to about 550° C. (1022° F.), preferably about 400° C. (752° F.) to about 550° C. (1022° F.), and more preferably at about 440° C. (824° F.) to about 460° C. (860° F.). The WHSV of this process is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$. At about 0.8 hr.$^{-1}$ to about 1.2 hr.$^{-1}$, approximately 98% to 100% conversion of the feed to hydrocarbons occurs.

The following examples serve to illustrate specific embodiments of the process of this invention, but should not be considered as a limitation on the scope of the invention.

EXAMPLE 1

Zeolites ZSM-5, having silica-to-Me$_2$O$_3$ molar ratios (silica-to-alumina molar ratios) of 35, 350, and 1000 (determined stoichiometrically), were produced as described in U.S. Pat. No. 3,702,886.

Each ZSM-5 was calcined at 510° C. (950° F.) and the calcined material was ion exchanged with an ammonium nitrate solution (85° C., 185° F.; 12 hours). Generally, the ion exchange was repeated two or three times, with a calcination at 510° C. (950° F.) between each ion exchange step.

The catalytic conversion of methanol or methanol/water to hydrocarbons using each ZSM-5 having a preselected silica-to-alumina ratio of 35, 350, and 1000 was carried out in a fixed bed (½", 1.27 cm diameter), stainless steel reactor, equipped with a ⅛" (0.32 cm) coiled preheater. In addition, the reactor was equipped with a ⅛" (0.32 cm) thermocouple well running axially through the reactor. The reactor was heated in an Applied Test Systems 3 zone tube furnace (12", 30.5 cm long; 1¼", 3.18 cm I.D.) having one reactor with three spaced zones. The first reactor zone is used as a preheater zone, and the catalyst bed is heated in the second reactor zone. The third reactor zone operates as a quench zone maintained at a temperature of about 200° C. (392° F.) to about 300° C. (572° F.).

Generally, 2 grams (0.07 ounces) catalyst (−14/+20 mesh) were mixed with 2.5 grams (0.09 ounces) of quartz (−20/+60); the first and third reactor zone were filled with quartz chips (−10/+20 mesh). To improve the heat transfer between the second reactor zone (containing the catalyst bed) and the furnace heating coils, the second reactor zone was equipped with a cylindrical (~4", 10.2 cm long; 1¼", 3.18 cm O.D.) aluminum or stainless steel block. This block contained a central hole in order to be able to measure the block temperature.

Gas flows (nitrogen or hydrogen) were controlled by mass flow controllers, while liquid feed rates were controlled by a Beckmann 114M pump or a Sage 341B syringe pump.

The product emerging from the reactor was analyzed on line for (i) carbon monoxide; carbon dioxide; water; dimethyl ether; methanol; $C_1$–$C_3$ hydrocarbons with a Porepack Q column using a thermal conductivity detector and (ii) $C_1$–$A_{10}$ hydrocarbons with a DB-1 column using a flame ionization detector. The feed was either methanol or methanol:water (1:1 or 1:4 molar ratio as denoted in Table I) at a WHSV=1.0 hr.$^{-1}$. The reaction was conducted at 450° C. (842° F.). The results are shown in Table I.

EXAMPLE 2

The zeolite ZSM-48, having a silica-to-$Me_2O_3$ molar ratio of 336 (determined by wet chemical analysis), was produced as described in U.S. Pat. No. 4,423,021.

ZSM-48 was calcined at 510° C. (950° F.) and the calcined material was ion exchanged with ammonium nitrate solution (85° C., 185° F.); 12 hours). Generally, the ion exchange was repeated two or three times, with a calcination at 510° C. (950° F.) between each ion exchange step.

The catalytic conversion of methanol or methanol/water to hydrocarbons was carried out in a fixed bed (½", 1.27 cm diameter), stainless steel reactor, equipped with a ⅛" (0.32 cm) coiled preheater. In addition, the reactor was equipped with a ⅛" (0.32 cm) thermocouple well running axially through the reactor. The reactor was heated in an Applied Test Systems 3 zone tube furnace (12", 30.5 cm long; 1¼", 3.18 cm I.D.) having one reactor with three spaced zones. The first reactor zone is used as a preheater zone, and the catalyst bed is heated in the second reactor zone. The third reactor zone operates as a quench zone maintained at a temperature of about 200° C. (392° F.) to about 300° C. (572° F.).

Generally, 2 grams (0.07 ounces) catalyst (−14/+20 mesh) were mixed with 2.5 grams (0.09 ounces) of quartz (−20/+60); the first and third reactor zones were filled with quartz chips (−10/+20 mesh). To improve the heat transfer between the second reactor zone (containing the catalyst bed) and the at a temperature of about 200° C. (392° F.) to about 300° C. (572° F.).

Generally, 2 grams (0.07 ounces) catalyst (−14/+20 mesh) were mixed with 2.5 grams (0.09 ounces) of quartz (−20/+60); the first and third reactor zones were filled with quartz chips (−10/+20 mesh). To improve the heat transfer between the second reactor zone (containing the catalyst bed) and the furnace heating coils, the second reactor zone was equipped with a cylindrical (~4", 10.2 cm long; 1¼", 3.18 cm O.D.) aluminum or stainless steel block. This block contained a central hole in order to be able to measure the block temperature.

Gas flows (nitrogen or hydrogen) were controlled by mass flow controllers, while liquid feed rates were controlled by a Beckmann 114M pump or a Sage 341B syringe pump.

The product emerging from the reactor was analyzed on line for (i) carbon monoxide; carbon dioxide; water; dimethyl ether; methanol; $C_1$–$C_3$ hydrocarbons with a Porepack Q column using a thermal conductivity detector and (ii) $C_1$–$A_{10}$ hydrocarbons with a DB-1 column using a flame ionization detector. The feed was methanol:water (1:1 molar ratio) at a WHSV=1.0 hr.$^{-1}$. The reaction was conducted at 450° C. (842° F.). The results are shown in Table I.

EXAMPLE 4

SAPO-34 was calcined at 510° C. (950° F.) and the calcined material was ion exchanged with an ammonium nitrate solution (85° C., 185° F.; 12 hours). Generally, the ion exchange was repeated two or three times, with a calcination at 510° C. (950° F.) between each ion exchange step.

The catalytic conversion of methanol or methanol/water to hydrocarbons was carried out in a fixed bed (½", 1.27 cm diameter), stainless steel reactor, equipped with a ⅛" (0.32 cm) coiled preheater. In addition, the reactor was equipped with a ⅛" (0.32 cm) thermocouple well running axially through the reactor. The reactor was heated in an Applied Test System 3 zone tube furnace (12", 30.5 cm long; furnace heating coils, the second reactor zone was equipped with a cylindrical (~4", 10.2 cm long; 1¼", 3.18 cm O.D.) aluminum or stainless steel block. This block contained a central hole in order to be able to measure the block temperature.

Gas flows (nitrogen or hydrogen) were controlled by mass flow controllers, while liquid feed rates were controlled by a Beckmann 114M pump or a Sage 341B syringe pump.

The product emerging from the reactor was analyzed on line for (i) carbon monoxide; carbon dioxide; water; dimethyl ether; methanol; $C_1$–$C_3$ hydrocarbons with a Porepack Q column using a thermal conductivity detector and (ii) $C_1$–$A_{10}$ hydrocarbons with a DB-1 column using a flame ionization detector. The feed was methanol:water (1:1 molar ratio) at a WHSV=1.0 hr.$^{-1}$. The reaction was conducted at 450° C. (842° F.). The results are shown in Table I.

EXAMPLE 3

The zeolite FeZSM-5, having a silica-to-$Me_2O_3$ ratio of 350 (determined stoichiometrically), was produced as described in U.S. Pat. No. 4,843,183.

FeZSM-5 was calcined at 510° C. (950° F.) and the calcined material was ion exchanged with an ammonium nitrate solution (85° C., 185° F.; 12 hours). Generally, the ion exchange was repeated two or three times, with a calcination at 510° C. (950° F.) between each ion exchange step.

The catalytic conversion of methanol or methanol/water to hydrocarbons was carried out in a fixed bed (½", 1.27 cm diameter), stainless steel reactor, equipped with a ⅛" (0.32 cm) coiled preheater. In addition, the reactor was equipped with a ⅛" (0.32 cm) thermocouple well running axially through the reactor. The reactor was heated in an Applied Test System 3 zone tube furnace (12", 30.5 cm long; 1¼", 3.18 cm I.D.) having one reactor with three spaced zones. The first reactor zone is used as a preheater zone, and the catalyst bed is heated in the second reactor zone. The third reactor zone operates as a quench zone maintained 1¼", 3.18 cm I.D.) having one reactor with three spaced zones. The first reactor zone is used as a preheater zone, and the catalyst bed is heated in the second reactor zone. The third reactor zone operates as a quench zone maintained at a temperature of about 200° C. (392° F.) to about 300° C. (572° F.).

Generally, 2 grams (0.07 ounces) catalyst (−14/+20 mesh) were mixed with 2.5 grams (0.09 ounces) of quartz (−20/+60); the first and third reactor zones were filled with quartz chips (−10/+20 mesh). To improve the heat transfer between the second reactor zone (containing the catalyst bed) and the furnace heating coils, the second reactor zone was equipped with a cylindrical (~4", 10.2 cm long; 1¼", 3.18 cm O.D.) aluminum or stainless steel block. This block contained a central hole in order to be able to measure the block temperature.

Gas flows (nitrogen or hydrogen) were controlled by mass flow controllers, while liquid feed rates were controlled by a Beckmann 114M pump or a Sage 341B syringe pump.

The product emerging from the reactor was analyzed on line for (i) carbon monoxide; carbon dioxide; water; dimethyl ether; methanol; $C_1$–$C_3$ hydrocarbons with a Porepack Q column using a thermal conductivity detector and (ii) $C_1$–$A_{10}$ hydrocarbons with a DB-1 column using a flame ionization detector. The feed was methanol:water (1:4 molar ratio) at a WHSV=1.0 hr.$^{-1}$. The reaction was conducted at 450° C. (842° F.).

The results are shown in Table I.

TABLE I

Polymer-Grade Propylene Production

| Molecular Sieve | Silica-to-$Me_2O_3$ | Feed/Diluent (molar ratio) | Propane/propylene $C_3°/C_3=$ |
|---|---|---|---|
| ZSM-5 | 35 | Methanol/Water (1:1) | 0.770 |
| ZSM-5 | 1000 | Methanol (NA) | 0.044 |
| ZSM-5 | 350 | Methanol/Water (1:4) | 0.037 |
| ZSM-5 | 1000 | Methanol/Water (1:1) | 0.000 |
| ZSM-48 | 336 | Methanol/Water (1:1) | 0.038 |
| Fe ZSM-5 | 350 | Methanol/Water (1:1) | 0.039 |
| SAPO-34 | NA* | Methanol/Water (1:4) | 0.001 |

*NA signifies "not applicable."

As shown in Table I, olefins are formed by contacting the oxygenate feed with a molecular sieve at a temperature of between 350° C. (662° F.) to 550° C. (1022° F.). By preselecting the silica-to-$Me_2O_3$ ratio and/or diluent, a product having a propane/propylene ratio characteristic of high purity olefins can be produced. This can be achieved without the need of superfractionation to remove propane.

Many other variations and modifications may be made in the techniques herein before described, by those having experience in this technology, without departing from the concept of the present invention. Accordingly, it should be clearly understood that the methods described in the foregoing description are illustrative only and not intended as a limitation on the scope of the invention.

What is claimed is:

1. A process for making an olefin product for the production of plastic, comprising:

providing an oxygenate feed which comprises methanol;

contacting the oxygenate feed with a SAPO-34 molecular sieve catalyst under conditions effective to convert the oxygenate feed to an olefin-containing composition, wherein the effective conditions include a weight hourly space velocity (WHSV) of from 0.01 hr$^{-1}$ to 100 hr$^{-1}$, and a temperature of from 350° C. to 550° C.; and separating and recovering olefin product from the olefin-containing composition without subsequent removal of paraffins having the same number of carbon atoms as olefins from the olefin product, wherein the olefin product has a paraffin-to-olefin weight ratio of less than or equal to about 0.05; and producing plastic from the olefin product.

2. The process of claim 1, wherein the olefin product comprises propane as the paraffin and propylene as the olefin.

3. The process of claim 2, wherein the olefin product comprises propylene at a range of from 95% to 99.5 weight percent.

4. The process of claim 2, wherein the olefin product comprises propylene at above 99 weight percent.

5. The process of claim 1, wherein said temperature is from 400° C. to 550° C.

6. The process of claim 1, wherein said WHSV is from 0.5 hr$^{-1}$ to 10 hr$^{-1}$.

7. The process of claim 1, wherein the plastic is polypropylene.

* * * * *